United States Patent
Timme et al.

(10) Patent No.: US 10,780,005 B2
(45) Date of Patent: Sep. 22, 2020

(54) WARMING THERAPY PATIENT CARE UNITS WITH AUTOMATED WARM-UP MODES

(75) Inventors: Ulf Timme, Havertown, PA (US);
Harald Kneuer, Klingberg (DE);
Philip Moehring, Luebeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 792 days.

(21) Appl. No.: 14/352,981

(22) PCT Filed: Dec. 13, 2011

(86) PCT No.: PCT/US2011/064742
§ 371 (c)(1),
(2), (4) Date: Jun. 12, 2014

(87) PCT Pub. No.: WO2013/058799
PCT Pub. Date: Apr. 25, 2013

(65) Prior Publication Data
US 2014/0303694 A1    Oct. 9, 2014

Related U.S. Application Data

(60) Provisional application No. 61/550,289, filed on Oct. 21, 2011.

(51) Int. Cl.
*A61F 7/00* (2006.01)
*A61G 11/00* (2006.01)
(Continued)

(52) U.S. Cl.
CPC ............ *A61G 11/00* (2013.01); *A61F 7/0053* (2013.01); *A61M 16/0003* (2014.02);
(Continued)

(58) Field of Classification Search
CPC .... A61G 11/00; A61G 10/00; A61G 2203/46; A61M 16/0003; A61M 21/0094;
(Continued)

(56) References Cited

U.S. PATENT DOCUMENTS 4,034,740 A * 7/1977 Atherton ................ A61G 11/00
219/400
5,817,003 A * 10/1998 Moll ...................... A61G 11/00
600/22
(Continued)

FOREIGN PATENT DOCUMENTS

EP    0862901 A1    9/1998
EP    1124169 A2    8/2001
(Continued)

OTHER PUBLICATIONS

Barbieri, L, Robert, "Therapeutic hypothermia for newborns who suffer hypoxicischemic birth injury" OBG Management vol. 22 No. 11 (2010).
(Continued)

*Primary Examiner* — Linda C Dvorak
*Assistant Examiner* — Yasamin Ekrami
(74) *Attorney, Agent, or Firm* — McGlew and Tuttle, P.C.

(57) ABSTRACT

Described herein is a system including a patient support unit having a patient environment, a heating module, a sensor module, and a control system. The control system is configured to selectively operate the system in a pre-programmed warm-up mode configured to gradually warm the patient in the patient environment according to a series of stepped skin temperature increases performed over a series of stepped time durations to achieve a goal skin temperature. Related apparatus, system, methods and/or articles are described.

32 Claims, 5 Drawing Sheets

(51) Int. Cl.
    *G05D 22/02*     (2006.01)
    *G05D 23/19*     (2006.01)
    *G05D 27/02*     (2006.01)
    *A61M 16/00*     (2006.01)
    *A61M 16/10*     (2006.01)
    *A61M 16/20*     (2006.01)

(52) U.S. Cl.
    CPC ...... *A61M 16/0051* (2013.01); *A61M 16/024* (2017.08); *A61M 16/1015* (2014.02); *A61M 16/202* (2014.02); *G05D 22/02* (2013.01); *G05D 23/1919* (2013.01); *G05D 27/02* (2013.01); *A61F 2007/0064* (2013.01); *A61F 2007/0071* (2013.01); *A61F 2007/0093* (2013.01); *A61F 2007/0094* (2013.01); *A61F 2007/0095* (2013.01); *A61G 2200/327* (2013.01); *A61G 2203/46* (2013.01); *A61G 2210/30* (2013.01); *A61G 2210/90* (2013.01); *A61M 2016/1025* (2013.01)

(58) Field of Classification Search
    CPC ................ A61M 16/202; A61F 7/0053; A61F 2007/0093; A61F 2007/0095; A61F 2007/0094; A61F 2007/009; G05D 23/1919
    See application file for complete search history.

(56) References Cited

U.S. PATENT DOCUMENTS

| | | |
|---|---|---|
| 5,871,526 A | 2/1999 | Gibbs et al. |
| 6,254,525 B1 | 7/2001 | Reinhardt et al. |
| RE38,453 E | 3/2004 | Lessard et al. |
| 6,719,780 B1 | 4/2004 | Salmon et al. |
| 7,059,323 B2* | 6/2006 | Kullik ............... A61G 10/04 128/202.12 |
| 2002/0000234 A1* | 1/2002 | Manker ................ A61B 18/18 128/898 |
| 2002/0095198 A1* | 7/2002 | Whitebook ....... A61M 25/0017 607/100 |
| 2002/0147381 A1 | 10/2002 | Kolarovic |
| 2002/0161276 A1 | 10/2002 | Mountain |
| 2003/0197003 A1 | 10/2003 | Kneuer |
| 2004/0064171 A1 | 4/2004 | Briscoe et al. |
| 2004/0215052 A1 | 10/2004 | Kullik et al. |
| 2007/0135675 A1 | 6/2007 | MacKin et al. |
| 2007/0149843 A1 | 6/2007 | Ten Eyck et al. |
| 2009/0149927 A1 | 6/2009 | Kneuer et al. |
| 2009/0240312 A1* | 9/2009 | Koewler ................ A61B 5/01 607/104 |

FOREIGN PATENT DOCUMENTS

| | | |
|---|---|---|
| EP | 1800641 A2 | 6/2007 |
| JP | 2003126275 A | 5/2003 |
| WO | WO-2008142650 A1 | 11/2008 |

OTHER PUBLICATIONS

International Search Report and Written Opinion in PCT/US2011/064737 dated Jun. 26, 2012.
International Search Report and Written Opinion in PCT/US2011/064742 dated Jun. 22, 2012.
International Search Report and Written Opinion of PCT/US2011/064739 dated Jun. 26, 2012.
Patton, Sarah B. "Weaning Thermoregulatory Support in Preterm Neonates" University of Missoui-Columbia Internet Article. (2008) pp. 1-5.

* cited by examiner

WARMING THERAPY PATIENT CARE UNITS WITH AUTOMATED WARM-UP MODES

REFERENCE TO PRIORITY DOCUMENT

This application claims the benefit of priority under 35 U.S.C. § 119(e) of U.S. Provisional Patent Application Ser. No. 61/550,289, filed Oct. 21, 2011. Priority of the aforementioned filing date is hereby claimed and the disclosure of the provisional patent application is hereby incorporated by reference in its entirety.

TECHNICAL FIELD

The subject matter described herein relates to automatically monitoring and controlling the rate of temperature change of in an incubator or warmer environment.

BACKGROUND

Medical incubators and warmers are typically used to provide heat support to patients, such as premature infants, who cannot maintain their own body temperature. Closed incubators produce the necessary climate including temperature, relative humidity and oxygen content. Open care units and warmers generally only provide temperature regulation usually with heat radiation source and conductive heated mattress.

SUMMARY

In one aspect, provided is a system including a patient support unit having a patient environment, a heating module having a heater and a heating module controller operatively coupled to the heater. The heater is configured to warm the patient environment. The system includes a sensor module having a skin temperature sensor and a skin temperature controller operatively coupled to the skin temperature sensor and to the heater. The skin temperature sensor is configured to measure a skin temperature of a patient in the patient environment. The system includes a control system having at least one processor, at least one memory coupled to the at least one processor and including at least one program stored thereon, and at least one input interface. The control system is configured to selectively operate the system in a pre-programmed warm-up mode configured to gradually warm the patient in the patient environment according to a series of stepped skin temperature increases performed over a series of stepped time durations to achieve a goal skin temperature.

The heating module controller can be regulated by the control system to supply adequate heat from the heater to achieve a skin temperature set-point within one in the series of stepped time durations. The skin temperature set-point can equal the skin temperature of the patient measured at a start of one in the series of stepped time durations plus one in the series of stepped temperature increases. Warm-up mode can end once the skin temperature of the patient measured equals the goal skin temperature. The goal skin temperature can be between about 34° C. to 38° C. Each in the series of stepped skin temperature increases can be between about 0.1° C. to 1.0° C. Each in the series of stepped time durations can be at least about 2, 4, 6, 8, 10, 12, 15, 18, 20, 22, 25, 28, or 30 minutes.

The system can further include an environmental sensor module having one or more air temperature sensors. The one or more air temperature sensors can be configured to measure air temperature within the patient environment, which can be closed. The one or more air temperature sensors can be operationally coupled to an air temperature controller. The environmental sensor module can further include one or more oxygen sensors configured to measure oxygen content within the patient environment. The one or more oxygen sensors can be coupled to a servo oxygen controller operationally coupled to an oxygen valve configured to deliver controlled amounts of oxygen to the patient environment. The environmental sensor module can further include one or more humidity sensors. The one or more humidity sensors can be coupled to a humidity heater and a humidity controller configured control the humidity heater to regulate moisture content in the patient environment. The heater can include one or more of a main air heater, a mattress heater, a radiant heater, or a humidity heater. The patient can be a premature or full-term newborn baby.

In an interrelated aspect, provided is a method including supporting a patient in a patient environment of an incubator. The incubator includes a heating module having a heater and a heating module controller operatively coupled to the heater. The heater is configured to warm the patient environment. The incubator includes a sensor module having a skin temperature sensor and a skin temperature controller operatively coupled to the skin temperature sensor and to the heater. The skin temperature sensor is configured to measure a skin temperature of the patient in the patient environment. The incubator includes a control system having at least one display, at least one processor, at least one memory coupled to the at least one processor and including at least one program stored thereon, and at least one input interface. The method further includes receiving a command by the control system to perform a pre-programmed warm-up mode protocol configured to gradually warm the patient in the patient environment according to a series of stepped skin temperature increases performed over a series of stepped time durations to achieve a goal skin temperature.

The method can further include prompting a user on the display to identify one or more of the goal skin temperature, the stepped time durations, and the stepped skin temperature increases. The method can further include automatically measuring the current skin temperature of the patient using the skin temperature sensor and continuously communicating the measured current skin temperature to the control system. The method can further include automatically regulating the heater module to supply adequate heat from the heater to achieve a skin temperature set-point within one in the series of stepped time durations. The skin temperature set-point can equal the skin temperature of the patient measured at a start of one in the series of stepped time durations plus one in the series of stepped temperature increases. The method can further include comparing the skin temperature of the patient to the goal skin temperature over the step duration. The warm-up mode protocol can end once the skin temperature of the patient measured equals the goal skin temperature. The goal skin temperature can be between about 34° C. to 38° C. Each in the series of stepped skin temperature increases can be between about 0.1° C. to 1.0° C. Each in the series of stepped time durations can be at least about 2, 4, 6, 8, 10, 12, 15, 18, 20, 22, 25, 28, or 30 minutes.

The method can further include an environmental sensor module having one or more air temperature sensors. The one or more air temperature sensors can be configured to measure actual air temperature within the patient environment, which is closed. The one or more air temperature sensors can be operationally coupled to an air temperature controller. The environmental sensor module can further include one or more oxygen sensors. The one or more oxygen sensors can be coupled to a servo oxygen controller operationally coupled to an oxygen valve configured to deliver controlled amounts of oxygen to the patient environment. The environmental sensor module can further include one or more humidity sensors. The one or more humidity sensors can be coupled to a humidity heater and a humidity controller configured control the humidity heater to regulate moisture content in the patient environment. The heater can include one or more of a main air heater, a mattress heater, a radiant heater, or a humidity heater. The patient can be a premature or full-term newborn baby.

Articles of manufacture are also described that comprise computer executable instructions permanently stored on non-transitory computer readable media, which, when executed by a computer, causes the computer to perform operations herein. Similarly, computer systems are also described that may include a processor and a memory coupled to the processor. The memory may temporarily or permanently store (e.g., non-transitorily store, etc.) one or more programs that cause the processor to perform one or more of the operations described herein. In addition, methods described herein can be implemented by one or more data processors either within a single computing system or distributed among two or more computing systems.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Disclosed herein are devices, systems, articles, and methods to automatically control and monitor the temperature change and rate of warming (or cooling) provided by patient incubators and warmers.

It should be appreciated that the devices, systems, articles, and methods disclosed herein can be used for a variety of patient types and are not limited to neonates, infants or premature infants. Further, the devices, systems, articles, and methods described herein can be used with incubators having generally an enclosed treatment space or warmers having generally open treatment spaces.

System Components

Figure 1:
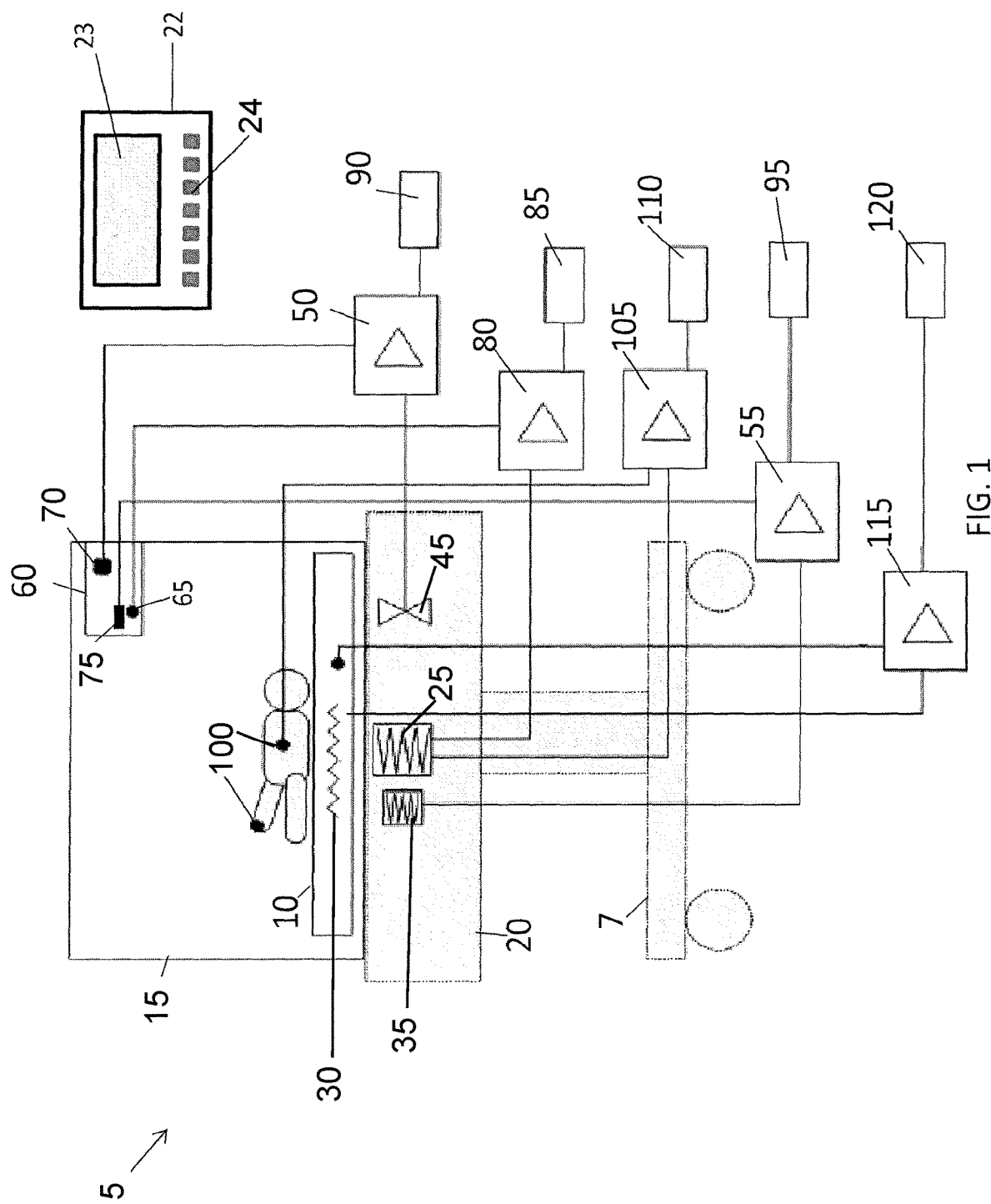
FIG. 1 is a box diagram illustrating an implementation of the system in an incubator.

FIG. 1 illustrates an implementation of a patient system 5 including a patient support unit including a lying surface such as a mattress 10 to support the patient that is surrounded at least in part by a hood 15. The system 5 can be positioned on a stand 7 or other support feature. The system 5 can include a heating module 20 that can include one or more heating units to direct warming energy for different purposes such as a main air heater 25, a mattress heater 30, and/or a humidity heater 35 or other air warmer. The mattress heater 30 can provide heat to the patient by contact between the patient and the mattress 10 or coverings surrounding the mattress 10. Mattress heater 30 can be operationally coupled to a mattress heater controller 115 that can be adjusted (manually and/or automatically) using the mattress temperature setting 120.

Figure 2:
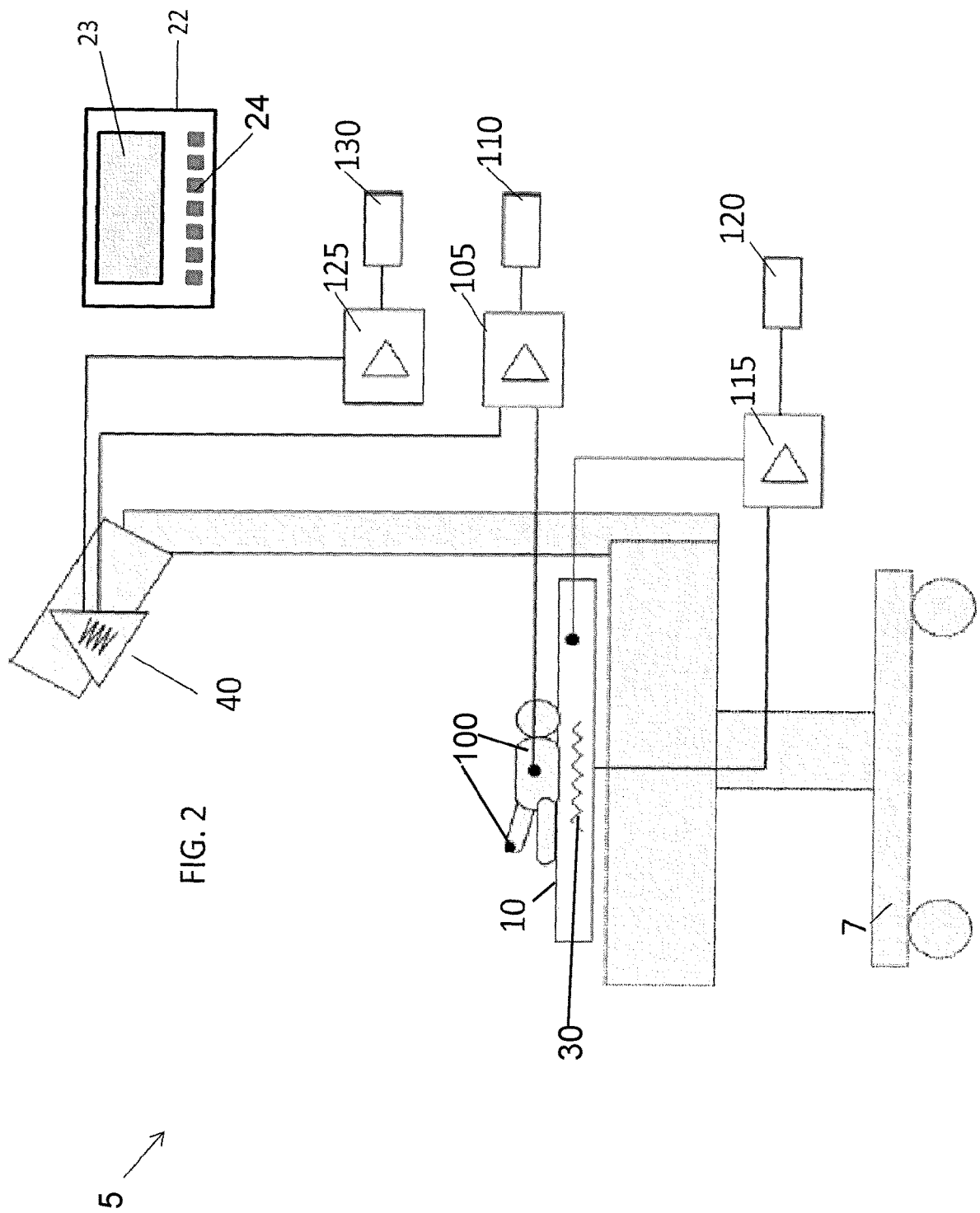
FIG. 2 is a box diagram illustrating another implementation of the system in an open warmer.

The heating module 20 can also include one or more radiant heaters 40 for providing heat to the patient by radiation. A radiant heater 40 is typically provided with warmers where the patient warmer has sidewalls but is open to the top for operation with a radiant heater 40 (see FIG. 2). Also as shown in FIG. 2, the radiant heater 40 can be operationally coupled to a radiant heater control 125 that can be adjusted (manually and/or automatically) using a heater power setting 130.

The climate of the patient environment can also be controlled for oxygen content and relative humidity. The system 5 can also include an oxygen valve 45 and servo oxygen controller 50 configured to deliver controlled amounts of oxygen to the patient environment. The system 5 can also include a humidity controller 55 that can control the humidity heater 35 to regulate the moisture content in the patient environment.

Control and monitoring of the system 5 can be provided using various sensing and control systems. Still with respect to FIG. 1, the system 5 can include an environmental sensor module 60 that can include one or more air temperature sensors 65, an oxygen sensors 70 and a humidity sensors 75. Air temperature sensor 65 can measure the actual air temperature in the closed patient environment. The air temperature sensor 65 can be operationally coupled to an air temperature controller 80. The air temperature controller 80 can be operationally coupled to the main heater 25 and can be adjusted (manually and/or automatically) using an air temperature setting 85. The oxygen sensor 70 can be operationally coupled to the servo oxygen controller 50. The servo oxygen controller 50 can be operationally coupled to the oxygen valve 45 and can be adjusted (manually and/or automatically) using an oxygen setting 90. Similarly, the humidity sensor 75 can be operationally coupled to the humidity controller 55. The humidity controller 55 can be operationally coupled to the humidity heater 35 and can be adjusted (manually and/or automatically) using a relative humidity (RH) setting 95

Still with respect to FIG. 1, the system 5 can include one or more patient skin temperatures sensors 100. The skin temperature sensors 100 can be operationally coupled to a skin temperature controller 105. The skin temperature controller 105 can be operationally coupled to the main heater 25 and can be adjusted (manually and/or automatically) using a skin temperature setting 110. A first skin temperature sensor 100 can be positioned on the patient to measure core temperature such as on the head, abdomen or lower back and a second skin temperature sensor 100 can be positioned to measure peripheral temperature such as on a hand or foot. It has been noted that hypothermia can be recognized in the case of highly premature or full-term newborn babies from an intense cooling of the periphery, while the core of the body is still within a normal range. The body can attempt to maintain the core temperature by reducing the blood flow to the periphery via vasoconstriction, thus reducing heat loss to the environment at the periphery. Hyperthermia can be recognized from a decrease in the peripheral temperature with rising core temperature of the body. The body has centralized the blood flow to the core in this case in order to heat to a higher temperature, and it throttles the blood flow to the periphery in order to save heat and to use it to heat the central organs. A subsiding fever can be recognized from the high core temperature of the body with a simultaneously high peripheral temperature. The body uses the large surface of the periphery to cool the core of the body by a corresponding release of heat.

The system 5 can also include various indicators and/or alarms to indicate status of the device. For example, an alarm can sound when a sensed condition (e.g. skin temperature, air temperature, oxygen, humidity, $CO_2$, etc.) is outside of a set range or limit. The indicator and/or alarm may be a visual indication, auditory indication, tactile indication, and the like.

The monitoring and control of the system 5 can be provided by a control system that can include at least one processor, at least one memory coupled to the at least one processor and including at least one program stored thereon. The control system can also include a user interface system 22 can include at least one display 23 including a graphical user interface (GUI). The display 23 can vary including LCD, LED, plasma, OLED, and the like. The display 23 can be interactive or touch-sensitive screen having an input device such as a touch screen, a capacitance screen, a resistive screen or the like. The user interface system 22 can include one or more inputs 24 such as fixed buttons associated with fixed functions or changeable functions such as soft keys associated with the display 23. The soft keys can provide functions wherein the function is displayed and the display can change providing different functions in different situations. The fixed input keys can also have a function that changes depending upon the display provided. The system 5 can include other inputs 24 such as a keyboard, mouse, bar code reader, or other input device that can be separate from the display 23. The system 5 can also have the capability to operatively couple to a secondary display such as a PC, laptop, mobile communication device, smartphone, or personal digital assistant and the like.

The display can provide information to the user such as current skin temperature from one or more of the temperature sensors, current air temperature, relative humidity, oxygen, heater module percent capacity, procedure or protocol being performed, operating mode, skin temperature goal, duration of intervals, and skin temperature increases per interval step, as well as other patient-specific information.

Various aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, the memory, at least one input device, and at least one output device such as a display.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Operational Modes

The systems 5 described herein can be configured to selectively operate in a variety of modes depending on the type of environmental control and monitoring desired. Although the systems 5 described herein are described as having automatic control and monitoring, it should be appreciated that the systems 5 are capable of being manually configured and operated by the user.

Figure 3:
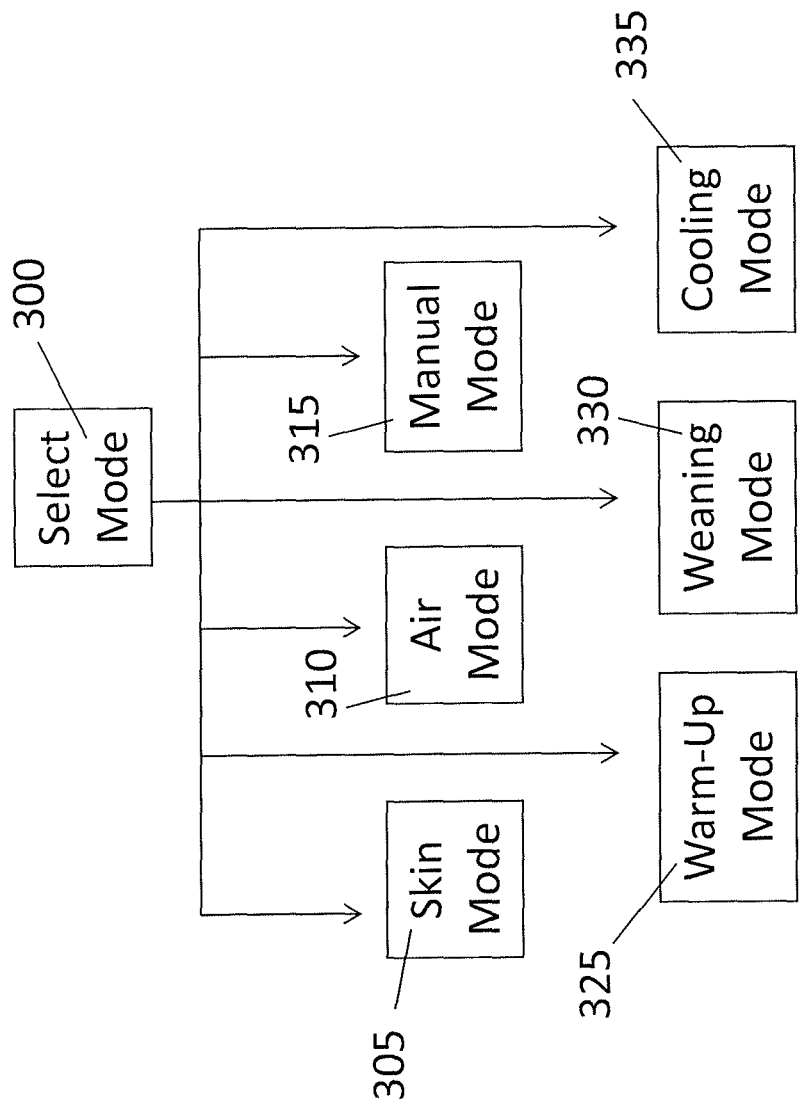
FIG. 3 is a box diagram illustrating various operational mode of the system.

FIG. 3 illustrates some of the modes of which the system 5 can operate. A user can be prompted by the system 5 to select a mode (300). The system 5 can be operated according Skin Mode (305), Air Mode (310), Manual Mode (315), Warm-Up Mode (325), Weaning Mode (330), and Cooling Mode (335). Control of the system 5 in Skin Mode 305 is based on achieving a desired skin temperature for the patient. A skin temperature sensor attached to the patient's skin can sense the actual skin temperature of the patient. The system 5 can regulate the heating module 20 to supply adequate heat to reach a desired skin temperature. The system 5 can regulate the heating module 20 based on various programmed protocols as will be described in more detail below. Control of the system 5 in Air Mode 310 is based on achieving a desired air temperature of the patient environment. The sensor module 60 of the system 5 can provide for measurement of the actual temperature inside the patient environment and regulate the heater module 20 to supply adequate heat to reach the desired air temperature. The automatic regulation can be based on various programmed protocols as will be described in more detail below.

Warm-Up Mode

In some situations, it can be desirable to warm a patient, particularly a premature or full-term newborn baby or neonate, gradually over a user-defined time period and according to a specific programmed protocol until a target skin temperature is achieved. Warm-Up Mode 325 can incorporate Skin Mode 305 temperature control. In Warm-up Mode 325, the skin temperature set-point is not fixed and can be automatically adjusted by the system 5 according to the protocol selected until the skin temperature reaches the goal skin temperature. The system 5 follows the user-defined protocol such that the user can selectively determine the rate at which warm-up occurs. The Warm-Up Mode 325 also allows a user to avoid manually increasing the heating power of a heater in the system to achieve the desired target skin temperature. The system 5 simplifies the warm-up procedure by providing an automatic mode to gradually warm a patient thereby increasing patient safety and time savings for medical care professionals.

Figure 4:
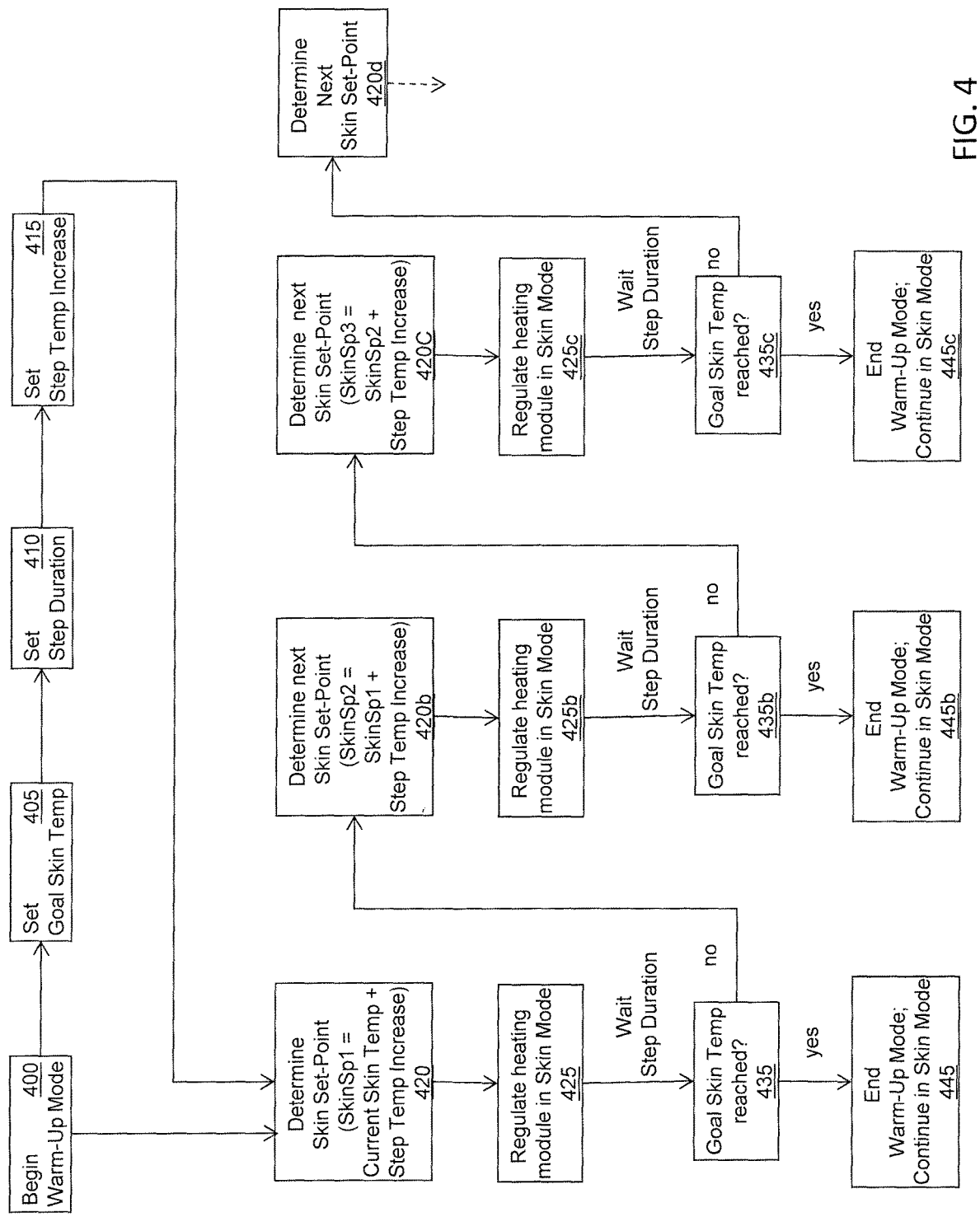
FIG. 4 is a flowchart illustrating a Warm-Up Mode operation.

FIG. 4 illustrates an example of a Warm-Up Mode operation. Upon start of the Warm-Up Mode 325, the system 5 can switch into Skin Mode 305. Warm-up Mode begins (400) and a user can be prompted to Set Goal Skin Temp (405), Set Step Duration (410) and Set Step Temp Increase (415). Set Goal Skin Temp (405), Set Step Duration (410) and Set Step Temp Increase (415) can also be pre-defined or pre-configured by the system and respectively bypassed by the user upon initiation of Warm-Up Mode 325. In some implementations, Goal Skin Temp can be between about 34° C. to 38°

C. In some implementations, Step Duration can be at least about 2, 4, 6, 8, 10, 12, 15, 18, 20, 22, 25, 28, 30 or more minutes. In some implementations, Step Temp Increase can be between about 0.1° C. to 1.0° C.

Upon initiation of Warm-Up Mode, the system 5 can Determine Skin Set-Point (420), which is equal to the Current Skin Temp+Step Temp Increase. The system automatically Regulates Heating Module in Skin Mode (425) for the defined Step Duration as described above. The system can monitor whether the Goal Skin Temp is reached (435). If the Goal Skin Temp has been reached, Warm-up Mode will end and the system 5 can continue operating in Skin Mode (445). If the Goal Skin Temp has not been reached, the system will determine the next Skin Set-Point (420*b*), which is equal to the SkinSp1+Step Temp Increase. The system Regulates Heating Module in Skin Mode (425*b*) for the defined Step Duration. The system monitor whether the Goal Skin Temp is reached (435*b*). If the Goal Skin Temp has been reached, Warm-up Mode will end and the system 5 can continue operating in Skin Mode (445*b*). If the Goal Skin Temp has not been reached, the system will determine the next Skin Set-Point (420*c*), which is equal to the SkinSp2+Step Temp Increase. The system Regulates Heating Module in Skin Mode (425*c*) for the defined Step Duration. The system can monitor whether the Goal Skin Temp is reached (435*c*). If the Goal Skin Temp has been reached, Warm-up Mode will end and the system 5 can continue operating in Skin Mode (445*c*). If the Goal Skin Temp has not been reached, the system will determine the next Skin Set-Point (420*d*) and the operation carries on as described above.

The display 23 can indicate to the user that the system 5 is in Warm-Up Mode 325 or that Warm-Up Mode 325 has ended. During Warm-up mode 325, Skin Mode alarm limits can apply and can generate respective alarms if the patient is not able to reach the desired temperature. It should be appreciated that the Warm-Up Mode 325 can be incorporated in open care warming therapy as well as with closed care warming therapy such as an incubator.

Weaning Mode

In some situations, it can be desirable to wean a baby from a warming environment gradually over time until a goal air temperature is achieved. Infants that are well and ready to be moved from the incubator, are typically weaned from the warming system based on age and gestation. Weaning Mode 330 allows for the air temperature of the incubator to be gradually scaled down according to a programmed protocol over a time until a certain air temperature is reached and the infant is able to maintain its skin temperature within an acceptable range. The skin temperature of the infant is monitored by the system for fluctuations of temperature outside of the acceptable range. Weaning Mode 330 provides for thermal challenges of the infant prior to transfer and in turn can reduce the risk caused by thermal stress when transferring from a closed warming environment to an open warming environment and beyond.

Weaning Mode 330 can incorporate Air Mode 310 temperature control. In Weaning Mode 330, the air temperature set-point is automatically adjusted according to the selected pre-programmed protocol and the skin temperature of the infant monitored until the air temperature goal is ultimately reached. Once the air temperature goal is reached without the skin temperature fluctuating outside the acceptable skin temperature range, the Weaning Mode 330 ends.

Figure 5:
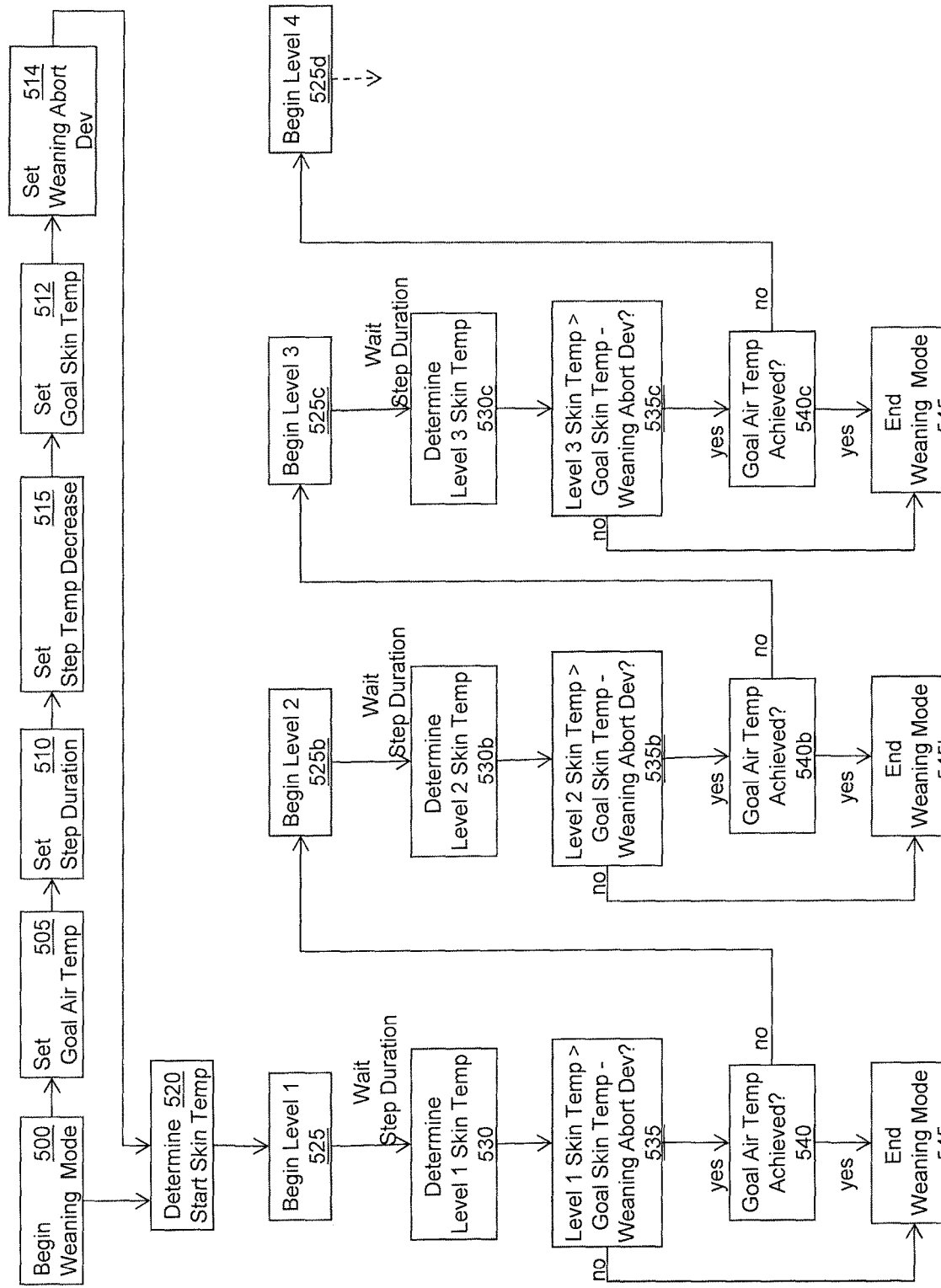
FIG. 5 is a flowchart illustrating a Weaning Mode operation.

FIG. 5 illustrates an example of a Weaning Mode operation. Upon start of the Weaning Mode 330, the system 5 can switch into Air Mode 310. Weaning Mode Begins (500) and a user is prompted to Set Goal Air Temp (505), Set Step Duration (510), Set Step Temp Decrease (515), Set Goal Skin Temp (512) and Set Weaning Abort Deviation (514). It should be appreciated that these parameters can also be pre-defined or pre-configured by the system and respectively bypassed by the user upon initiation of Weaning Mode 330. In some implementations, Goal Air Temp can be between about 20° C. to about 39° C. In some implementations, Step Duration can be at least about 1 hour to at least about 24 hours. In some implementations, Step Duration can be at least about 1, 2, 4, 8, 12, 18, and 24 hours. In some implementations, Step Temp Decrease can be between about 0.2° C. to 1.0° C. In some implementations, Goal Skin Temp can be between about 34.0° C. to 38.0° C. In some implementations, Weaning Abort Deviation can be between about 0.3° C. to 1.0° C.

Upon initiation of Weaning Mode 330, the system 5 Determine Start Skin Temp (520) and Begin Level 1 (525). The system 5 automatically regulates the heating module 20 to the Start Air Temp reduced by the Step Temp Decrease for the Step Duration to Begin Level 1 (525). Throughout the Weaning Mode procedure, the system 5 automatically monitors Skin Temp and assesses whether Skin Temp is equal to or greater than the Goal Skin Temp minus the Weaning Abort Deviation (535) to achieve the goal air temperature while maintaining the goal skin temperature within the weaning abort deviation range. If Level 1 Skin Temp lies outside the weaning abort deviation range, then the system 5 can End Weaning Mode (545) and/or an alarm can sound. The system 5 can switch back to the last temperature settings tolerated by the patient. If the Level 1 Skin Temp is within the deviation range, then the system 5 can assess whether the Goal Air Temp is achieved (540). If Goal Air Temp is achieved then the system 5 can End Weaning Mode (545) and a notification provided to the user. If Goal Air Temp is not achieved then the system 5 will Begin Level 2 (525*b*). The system 5 can automatically set the heating module 20 to the Level 1 Air Temp plus the Step Temp Decrease for the Step Duration to Begin Level 2 (525*b*). After the Step Duration, the system 5 can Determine Level 2 Skin Temp (530*b*) and assess whether Level 2 Skin Temp is greater than the Goal Skin Temp minus the Weaning Abort Deviation (535*b*). If Level 2 Skin Temp lies outside the deviation range, then the system 5 can End Weaning Mode (545*b*) and/or an alarm can sound. The system 5 can switch back to the last temperature settings tolerated by the patient. If the Level 2 Skin Temp is within the deviation range, then the system 5 can assess whether the Goal Air Temp is achieved (540*b*). If Goal Air Temp is achieved then the system 5 can End Weaning Mode (545*b*) and a notification provided to the user. If Goal Air Temp is not achieved then the system 5 will Begin Level 3 (525*c*). The system 5 can automatically set the heating module 20 to the Level 2 Air Temp plus the Step Temp Decrease for the Step Duration to Begin Level 3 (525*c*). After the Step Duration, the system 5 can Determine Level 3 Skin Temp (530*c*) and assess whether Level 3 Skin Temp greater than the Goal Skin Temp minus the Weaning Abort Deviation (535*c*). If Level 3 Skin Temp lies outside the deviation range, then the system 5 can End Weaning Mode (545*c*) and/or an alarm can sound. The system 5 can switch back to the last temperature settings tolerated by the patient. If the Level 3 Skin Temp is within the deviation range, then the system 5 can assess whether the Goal Air Temp is achieved (540*c*). If Goal Air Temp is achieved then the system 5 can End Weaning Mode (545*c*) and a notification provided to the user. If Goal Air Temp is not achieved then the system 5 will Begin Level 4 (525*d*) and the operation carries on as described above. It should be appreciated that the patient skin temperature is continually monitored. Thus, at any point during the Weaning Mode procedure if the patient skin temperature measured by the system falls outside the deviation range, the system 5 can End Weaning Mode (545) and/or an alarm can sound.

When the Air Temp Goal is reached, and the Skin Temp of the patient does not fall below the Weaning Abort Deviation, Weaning Mode 330 is disabled by the system 5, which can continue to operate in normal Air Mode 310. Further, a message can be provided on the display such as "weaning complete" after the selected weaning stabilization time is completed. Further, if humidity controller 55 or the mattress temperature controller 115 were enabled prior to the start of Weaning Mode 330, set-points for both humidity and mattress temperature can be set to auto mode.

Cooling Mode

In some situations, it can be desirable to cool a patient with an auxiliary device while the patient is still being monitored using the systems described herein. For example, newborns who suffer hypoxic-ischemic birth injury can be treated with whole-body cooling to limit neural damage and reduce the rate of neurological disorders such as cerebral palsy. An auxiliary device such as a cooling blanket or other device can be introduced to the system 5 to treat the patient. Cooling Mode 335 is a passive mode that can allow for the whole-body cooling of the patient while maintaining some of the patient-specific monitoring and data acquisition and avoiding nuisance alarms.

Cooling Mode 335 can incorporate patient and device monitoring similar to Air Mode 310 or Manual Mode 315. In Cooling Mode 335, the system automatically switches off the heating module 20 (or radiant heater 40, if used with a warmer) and mattress heater 30 and disables respective controls. The heater-related alarms (e.g. high/low air temperature alarm, mattress temperature deviations) can likewise be disabled by the system. In the incubator, the fan circulating air within the incubator enabling $CO_2$ washout, humidity control and servo oxygen control as well as the humidity controller 55, the servo oxygen controller 50 can all be maintained by the system during Cooling Mode 335. The Cooling Mode 335 allows for active patient cooling inside the system 5 and allows for patient-related data and skin temperature monitoring/alarming to continue while incubator heating and related alarms are avoided.

When used with open care warming therapy, the system 5 can switch into a Manual Mode 315. The radiant heater 40 and the optional mattress heater 30 can be switched off and their respective controls (radiant heat control 125 and heater power setting 130, mattress temperature controller 115 and setting 120) can be disabled while in Cooling Mode 335.

In one implementation, Cooling Mode 335 can be selected for start by the user and the system can switch into Air Mode 310 or Manual mode 315. One or more of the system heaters including the air heater 20, radiant heater 40, and/or mattress heater 30 can be disabled by the system as can the respective alarm monitoring mechanisms for the system heaters. A message such as "Cooling Mode" can be displayed to the user. The system provides for and monitors the protective environment including oxygen, humidity, and developmental care features during cooling including alarm limits as selected by the user. The system 5 leaves cooling mode upon selecting exit cooling mode.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Other embodiments can be within the scope of the claims.

What is claimed is:

1. A system comprising:
   a patient support unit having a patient environment;
   a heating module comprising a heater and a heating module controller operatively coupled to the heater, wherein the heater is configured to warm the patient environment;
   a sensor module comprising a skin temperature sensor and a skin temperature controller operatively coupled to the skin temperature sensor and to the heater, wherein the skin temperature sensor is configured to measure a skin temperature of a patient in the patient environment; and
   a control system comprising at least one processor, at least one memory coupled to the at least one processor and including at least one program stored thereon, and at least one input interface, wherein the control system is configured to selectively operate the system in a pre-programmed warm-up mode configured to gradually warm the patient in the patient environment according to a series of stepped skin temperature set-point increases automatically performed over a series of stepped time durations to achieve a goal skin temperature, wherein the goal skin temperature differs from each skin temperature set-point increases of the series of stepped skin temperature set-point increases, wherein each skin temperature set-point is automatically increased incrementally when the skin temperature has not reached the goal skin temperature after a time duration of the series of stepped time durations by a predetermined step temperature increase value and wherein warm-up mode ends automatically once the skin temperature of the patient measured equals the goal skin temperature,
   wherein the heating module controller is regulated by the control system to supply heat from the heater to have the skin temperature of the patient achieve each skin temperature set-point within a respective one of the series of stepped time durations, wherein the skin temperature set-point at a start of the series of stepped time duration equals a current skin temperature of the patient measured at a start of one of the series of stepped time durations plus the predetermined step temperature increase value.

2. The system of claim 1, wherein the goal skin temperature is between about 34° C. to 38° C.

3. The system of claim 1, wherein each in the series of stepped skin temperature set-point increases is between about 0.1° C. to 1.0° C.

4. The system of claim 1, wherein each in the series of stepped time durations is at least about 2, 4, 6, 8, 10, 12, 15, 18, 20, 22, 25, 28, or 30 minutes.

5. The system of claim 1, further comprising an environmental sensor module comprising one or more air temperature sensors.

6. The system of claim 5, wherein the one or more air temperature sensors are configured to measure air temperature within the patient environment, and wherein the patient environment is closed.

7. The system of claim 5, wherein the one or more air temperature sensors are operationally coupled to an air temperature controller.

8. The system of claim 5, wherein the environmental sensor module further comprises one or more oxygen sensors configured to measure oxygen content within the patient environment.

9. The system of claim 8, wherein the one or more oxygen sensors are coupled to a servo oxygen controller operationally coupled to an oxygen valve configured to deliver controlled amounts of oxygen to the patient environment.

10. The system of claim 5, wherein the environmental sensor module further comprises one or more humidity sensors.

11. The system of claim 10, wherein the one or more humidity sensors are coupled to a humidity heater and a humidity controller configured control the humidity heater to regulate moisture content in the patient environment.

12. The system of claim 1, wherein the heater comprises one or more of a main air heater, a mattress heater, a radiant heater, or a humidity heater.

13. The system of claim 1, wherein the patient comprises a premature or full-term newborn baby.

14. The system of claim 1, wherein information indicating warm-up mode has ended is provided to a user via the at least one display of a user interface system upon warm-up mode ending.

15. A method comprising:
supporting a patient in a patient environment of an incubator, wherein the incubator comprises:
a heating module comprising a heater and a heating module controller operatively coupled to the heater, wherein the heater is configured to warm the patient environment;
a sensor module comprising a skin temperature sensor and a skin temperature controller operatively coupled to the skin temperature sensor and to the heater, wherein the skin temperature sensor is configured to measure a skin temperature of the patient in the patient environment; and
a control system comprising at least one display, at least one processor, at least one memory coupled to the at least one processor and including at least one program stored thereon, and at least one input interface;
receiving a command by the control system to perform a pre-programmed warm-up mode protocol configured to gradually warm the patient in the patient environment according to a series of stepped skin temperature set-point increases automatically performed over a series of stepped time durations to achieve a goal skin temperature, wherein the goal skin temperature differs from each skin temperature set-point of the series of stepped skin temperature set-point increases wherein each skin temperature set-point is automatically increased incrementally when the skin temperature has not reached the goal skin temperature after a time duration of the series of stepped time durations by a predetermined step temperature increase value and wherein warm-up mode ends automatically once the skin temperature of the patient measured equals the goal skin temperature; and
automatically regulating the heater module to supply heat from the heater to have the skin temperature of the patient achieve each skin temperature set-point within a respective one of the series of stepped time durations, wherein the skin temperature set-point at a start of one of the series of stepped time durations equals a current skin temperature of the patient measured at a start of one of the series of stepped time durations plus the predetermined step temperature increase value.

16. The method of claim 15, further comprising prompting a user on the at least one display to identify one or more of the goal skin temperature, the stepped time durations, and the stepped skin temperature set-point increases.

17. The method of claim 15, further comprising automatically measuring the current skin temperature of the patient using the skin temperature sensor and continuously communicating the measured current skin temperature to the control system.

18. The method of claim 15, further comprising comparing the skin temperature of the patient to the goal skin temperature over the step duration.

19. The method of claim 15, wherein the goal skin temperature is between about 34° C. to 38° C.

20. The method of claim 15, wherein each in the series of stepped skin temperature set-point increases is between about 0.1° C. to 1.0° C.

21. The method of claim 15, wherein each in the series of stepped time durations is at least about 2, 4, 6, 8, 10, 12, 15, 18, 20, 22, 25, 28, or 30 minutes.

22. The method of claim 15, further comprising an environmental
sensor module comprising one or more air temperature sensors.

23. The method of claim 22, wherein the one or more air temperature sensors are configured to measure actual air temperature within the patient environment, and wherein the patient environment is closed.

24. The method of claim 22, wherein the one or more air temperature sensors are operationally coupled to an air temperature controller.

25. The method of claim 22, wherein the environmental sensor module further comprises one or more oxygen sensors.

26. The method of claim 25, wherein the one or more oxygen sensors are coupled to a servo oxygen controller operationally coupled to an oxygen valve configured to deliver controlled amounts of oxygen to the patient environment.

27. The method of claim 22, wherein the environmental sensor module further comprises one or more humidity sensors.

28. The method of claim 27, wherein the one or more humidity sensors are coupled to a humidity heater and a humidity controller configured control the humidity heater to regulate moisture content in the patient environment.

29. The method of claim 15, wherein the heater comprises one or more of a main air heater, a mattress heater, a radiant heater, or a humidity heater.

30. The method of claim 15, wherein the patient comprises a premature or full-term newborn baby.

31. The method of claim 15, wherein information indicating warm-up mode has ended is provided to a user via the at least one display of a user interface system upon warm-up mode ending.

32. A method of warming a patient in an incubator, the method comprising the steps of:
- setting a goal skin temperature of the patient;
- setting a stepped temperature increase;
- setting a stepped duration;
- measuring an actual skin temperature of skin of the patient during warming;
- setting a first duration temperature to the actual skin temperature of the patient plus the stepped temperature increase;
- heating the incubator during a first duration, the first duration having a length of time equal to the set stepped duration;
- regulating said heating during the first duration to have the actual skin temperature of the patient achieve the first duration temperature during the first duration;
- after the first duration, setting a second duration temperature to the actual skin temperature of the patient at the end of the first duration plus the stepped temperature increase;
- heating the incubator during a second duration after the first duration, the second duration having a length of time equal to the set stepped duration;
- regulating said heating of the incubator during the second duration to have the actual skin temperature of the patient achieve the second duration temperature;
- comparing the actual skin temperature with the goal skin temperature during said heating and said regulating;
- ending said heating when the actual skin temperature of the patient equals the goal skin temperature.

* * * * *